United States Patent [19]
Miller et al.

[11] 3,946,488
[45] Mar. 30, 1976

[54] REMOVABLE ORTHODONTIC APPLIANCE

[76] Inventors: Frank R. Miller, 1381 N. San Gabriel Canyon Road, Azusa, Calif. 91702; Craig A. Andreiko, 517 N. Holliston, Pasadena; John H. Di Giulio, 5623 Marshburn Ave., Arcadia, both of Calif. 91106

[22] Filed: Oct. 25, 1974

[21] Appl. No.: 517,999

[52] U.S. Cl. ............................................... 32/14 B
[51] Int. Cl.² ........................................... A61C 7/00
[58] Field of Search ......................................... 32/14

[56] References Cited
UNITED STATES PATENTS

| | | | |
|---|---|---|---|
| 3,089,242 | 5/1963 | Weissman | 32/14 A |
| 3,128,552 | 4/1964 | Broussard | 32/14 A |
| 3,464,113 | 9/1969 | Silverman et al. | 32/14 A |

*Primary Examiner*—Robert Peshock
*Attorney, Agent, or Firm*—Jessup & Beecher

[57] ABSTRACT

A two-part orthodontic appliance having a pedestal which is relatively permanently attached to a tooth, as by direct bonding or by a tooth band, and a bracket which is firmly but removably secured to the pedestal. A wide variety of lug configurations may be provided on the bracket, so that the appropriate bracket may be selected for the particular patient and tooth in question, as the orthodontic treatment proceeds over the weeks and months. The bracket may be readily replaced with one of another configuration to accommodate the changing forces that are needed to bring about the orthodontic correction. The bracket is secured to the pedestal by a locking member or detent formed from the bracket, which snaps into place over a detent edge formed on the pedestal. Removal of the bracket from the pedestal is accomplished by forcing the locking member back over the edge, and sliding the bracket off the pedestal.

10 Claims, 10 Drawing Figures

REMOVABLE ORTHODONTIC APPLIANCE

BACKGROUND OF THE INVENTION

As taught in the patent to Stifter, 2,908,974, it is quite useful to provide an orthodontic appliance in which a base is bonded to a tooth band which is carefully fitted over a tooth to be treated. The base is adapted to receive any of a large number of brackets, each having a different and unique working configuration in the form of a variety of slots or lugs to achieve the desired orthodontic force or torque. As the treatment proceeds, the orthodontist need merely replace the bracket portion of the appliance, while using the same tooth band base, and with minimum effort and inconvenience to the patient.

In accordance with the present invention, means are provided for expeditiously interlocking the bracket to the base of pedestal, while still permitting ready removal and interchange of brackets.

BRIEF DESCRIPTION OF THE DRAWINGS

In the drawings

FIG. 1 is a perspective view of the complete appliance showing the bracket in exploded position ready to be slid onto the pedestal member, which is shown secured to a tooth band encircling a tooth.

FIG. 2 is a fragmentary view showing the bracket in place slid onto the pedestal.

FIG. 3 is a cross-sectional perspective taken on line 3—3 in FIG. 2

FIG. 4 is a view, counterpart to FIG. 1, showing the bracket as it is actually fabricated into pieces, a base portion and a lug portion bonded together as by welding or brazing.

FIG. 5 is a fragmentary perspective view, counterpart to FIG. 2, showing the bracket in place on the pedestal.

FIG. 6 is a perspective section taken on line 6—6 in FIG. 5, being counterpart to FIG. 3.

FIG. 7 is a perspective counterpart to FIGS. 1 and 4.

FIG. 8 is a fragmentary perspective in section showing the bracket in place on the pedestal.

DETAILED DESCRIPTION OF THE EMBODIMENT OF THE INVENTION

Figure 1:
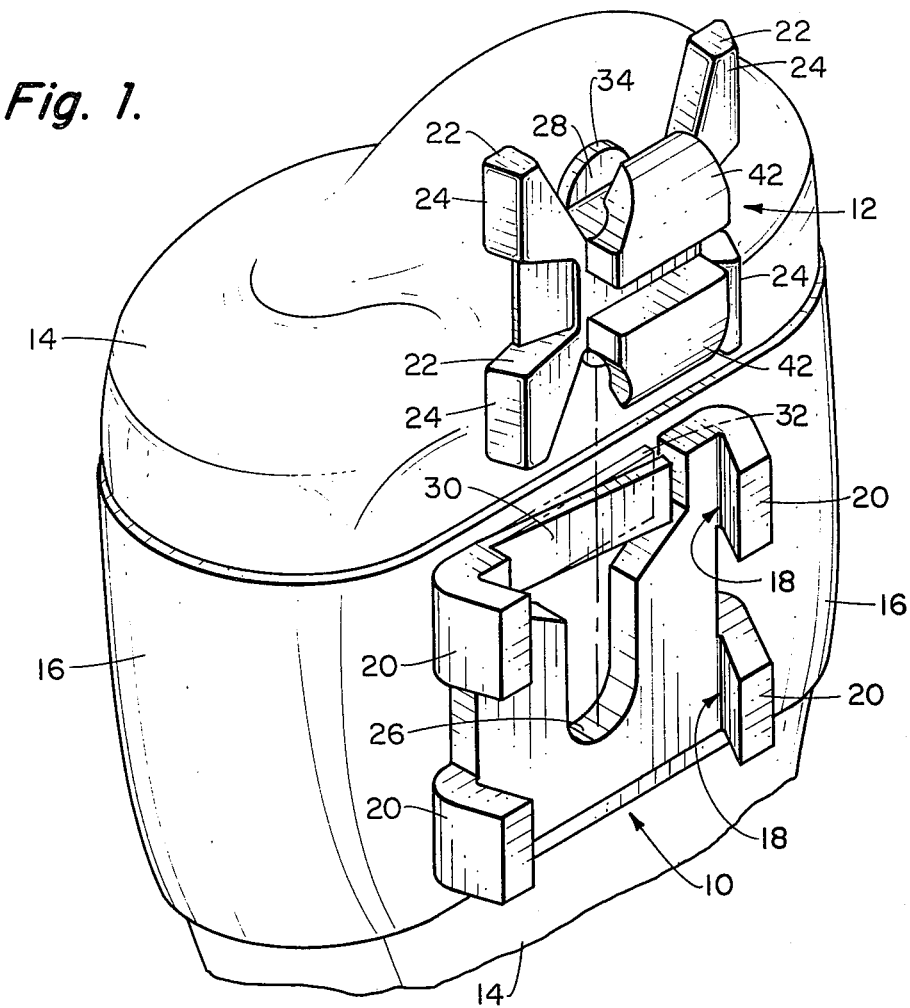
FIGS. 1, 2 and 3 illustrate a first species of this invention.
Figure 2:
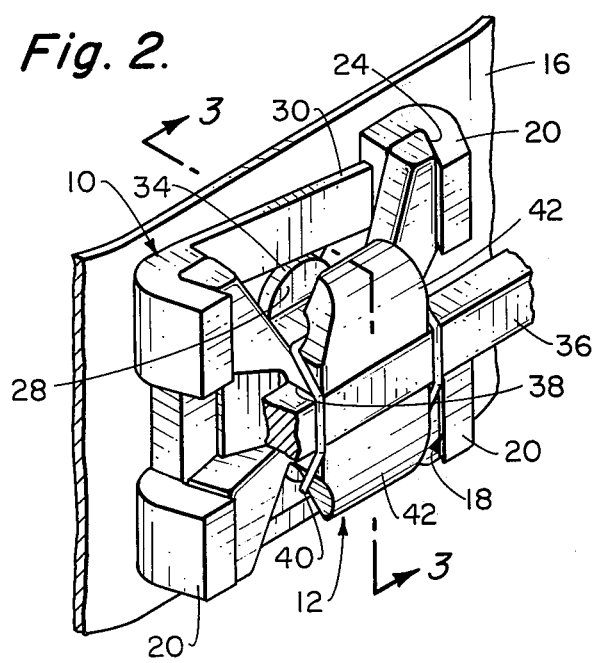
Figure 3:
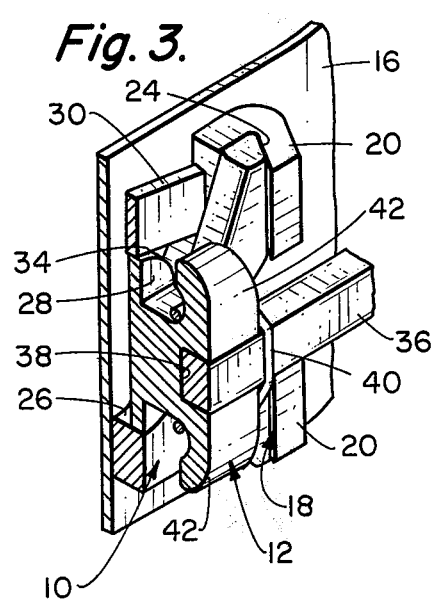

Referring to FIGS. 1–3, the appliance shown consists of a pedestal 10 and a bracket 12 adapted to be slideably mounted thereon. Pedestal 10 is shown secured to a tooth 14 by means of a tooth band 16 to which it is suitably bonded. Alternatively, the pedestal 10 may be direct bonded to the tooth 14.

The pedestal 10 is provided with a slide way 18 formed by pairs of in bent tabs 20 at each side of the pedestal.

The bracket 12 has four spider-like legs 22 provided with sloping faces 24 which form a slide that mates smoothly with the slide way 18 as the bracket 12 is slid onto the pedestal 10. In this way the bracket 12 may be readily applied to and removed from the tooth 14 without disturbing the basic securement consisting of the band 16 and the pedestal 10.

The slide 24 and slide way 18 are oriented in the incisalgingival direction. Along this same axis, the pedestal 10 is provided with a notch-like keyway 26, which receives a key 28 integrally formed on the bracket 12, as the bracket 12 is slid onto the pedestal 10. A flexible finger 30 is formed integrally from the pedestal 10 and extends transversely across the mouth or open end of the key way 26. It constitutes a locking member for holding the bracket 12 in place. All parts of the appliance are preferably formed of strong, somewhat resilient, material, such as stainless steel or a suitable plastic. Thus, the finger 30, being integrally formed from the pedestal 10 and free to flex slightly (as shown in phantom at 32), may be deflected to one side by the key 28 as the bracket 12 is slid onto the pedestal 10. As the key 28 seats in the key way 26, the finger 30 drops over the end of the key 28. Thus the end 34 of the key 28 constitutes a detent edge which, in cooperation with the the locking finger 30, serves to hold the bracket 12 in place on the pedestal 10.

The installed position of the bracket in the pedestal is shown in FIG. 2, which also illustrates that the bracket member 12 is provided with any suitable outer configuration for holding an arch wire 36 in place. Such configuration, for example, may assume the form of a groove 38, which receives the wire 36 and is held therein by ligatures 40 passing under suitable lugs 42.

Figure 4:
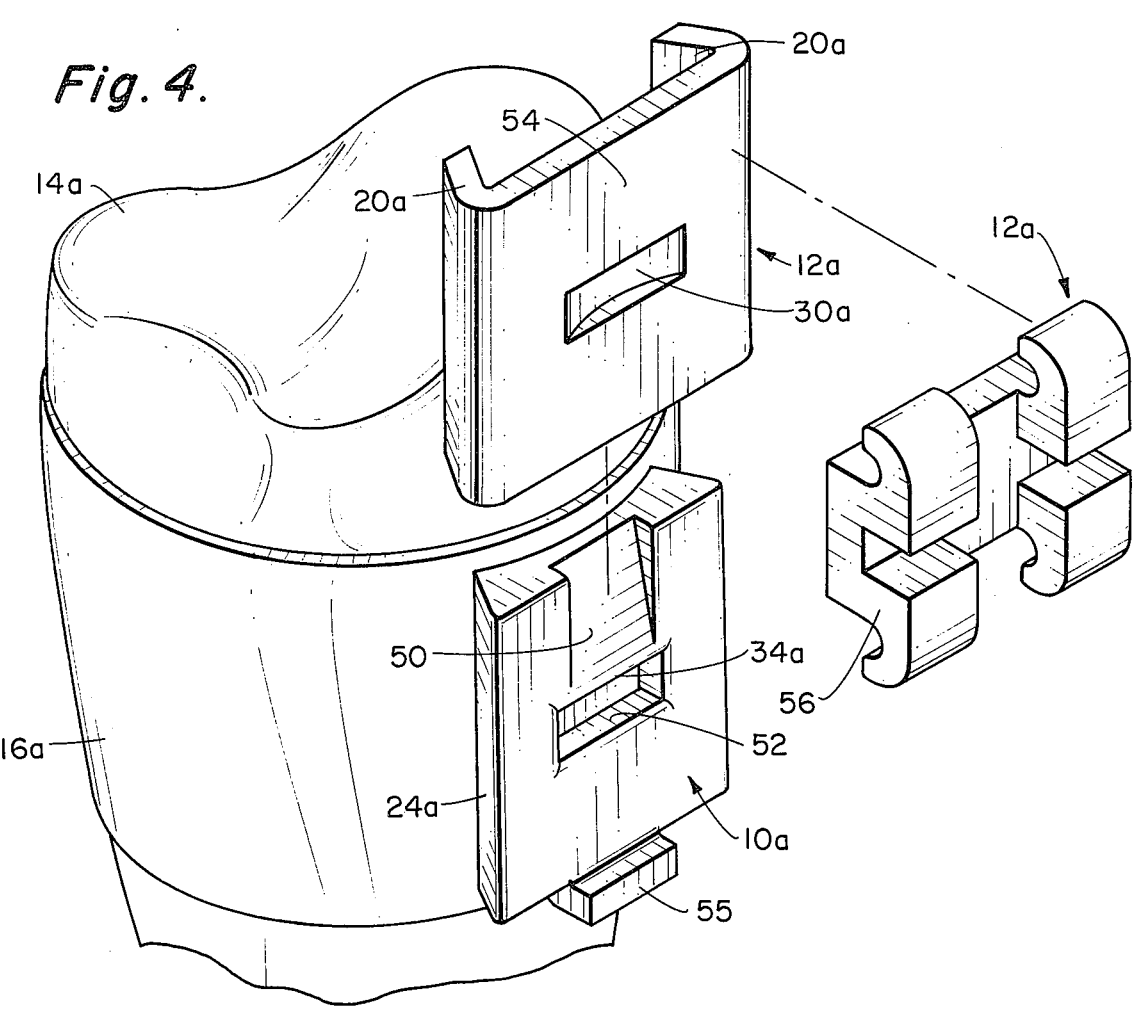
FIGS. 4, 5 and 6 show a second species of the invention.
Figure 5:
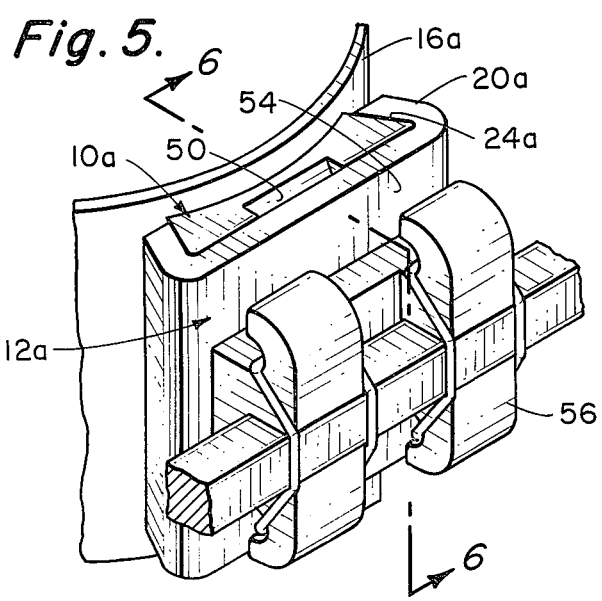
Figure 6:
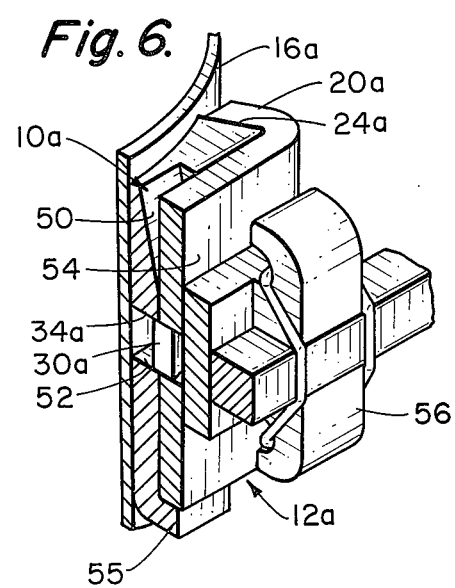

In FIGS. 4–6 a second form of invention is shown wherein the bracket member 12a contains the slide way in the form of in bent slide flanges 20a which receive the slide 24a formed by the bevelled edges on the side of the pedestal 10a, which is bonded to the tooth band 16a. In this form of the invention the locking detent member is formed by lancing out a transverse, elongate arced portion 30a, which retains its integral connection with the bracket 12a at each end, but is free of the parent metal in the center portion, and is thus free to flex or deflect slightly to lock the bracket 12a to the pedestal 10a. In this form, the entire body portions of both pedestal 10a and bracket 12a also bow outward slightly as the arc detent 30a rides up a ramp 50 before dropping into a centrally located recess 52 formed in the face of the pedestal 10a. Thus the flexing is a combination of this body flexing and the flexing of the lanced-out arc 30a in the bracket base 54.

The leading edge of the recess 52 forms a detent edge 34a that detentably locks the bracket 12a to the pedestal 10a. As the bracket 12a is slid onto the pedestal 10a, the sloping ramp 50 cams the lanced-out locking member 30a outward, causing the members 10a and 54 to bow away from each other. When arc 30a clears the edge 34a, it drops into locking position in recess 52. A further stop 55, bent integrally up from the end of the pedestal 10a, serves as an additional stop to retain the bracket 12a in position.

In the embodiment shown in FIGS. 4–6 the bracket 12a is formed in two parts, the relatively flat bracket base 54, and a bracket lug portion 56. They are suitable bonded together as by brazing.

Figure 7:
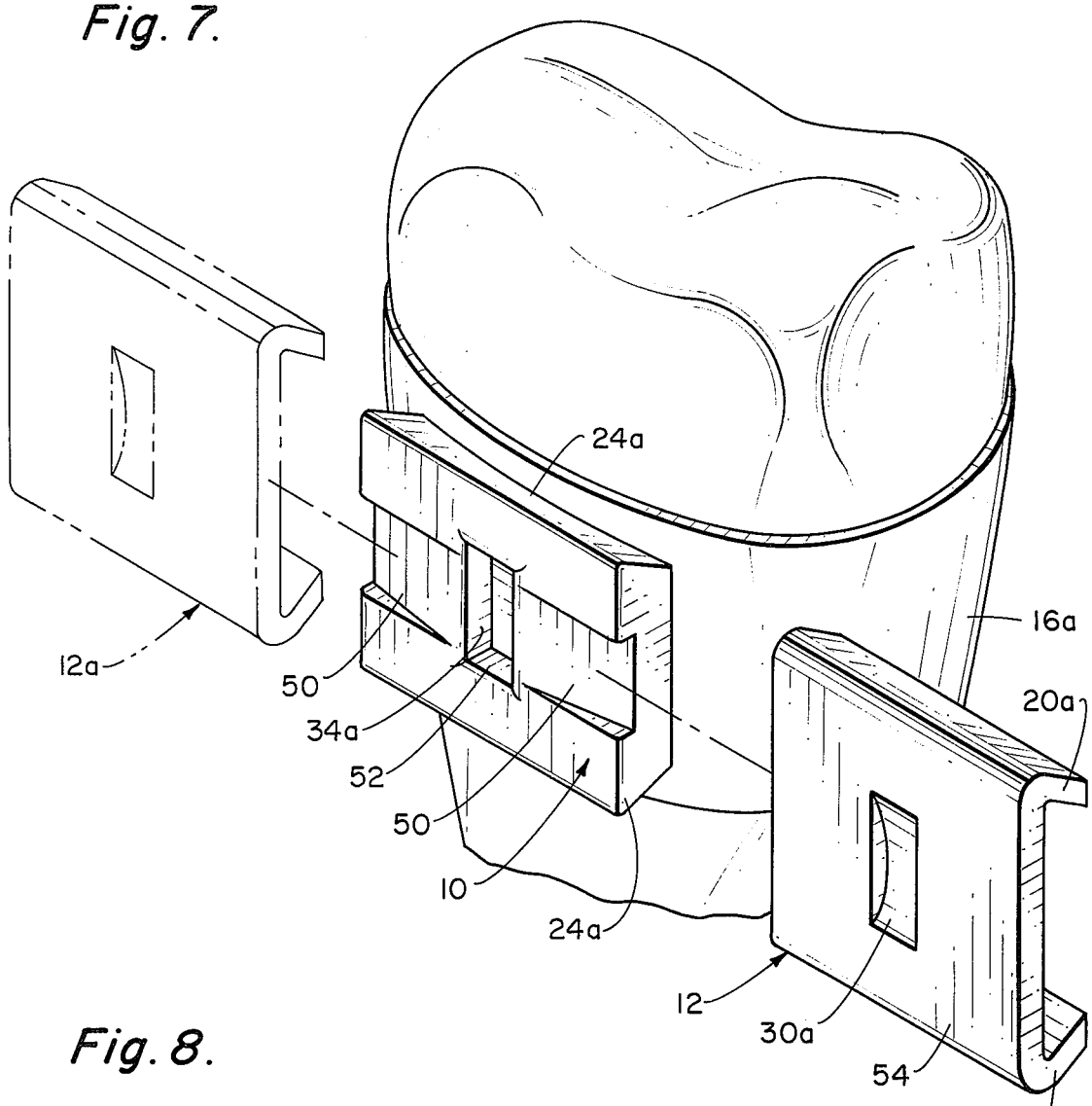
FIGS. 7 and 8 show a third species of the invention, being a variant on the species of FIGS. 4 – 6 in which the axis along which the bracket is slid onto the pedestal has been turned 90°, so that it lies on a mesial-distal axis.
Figure 8:
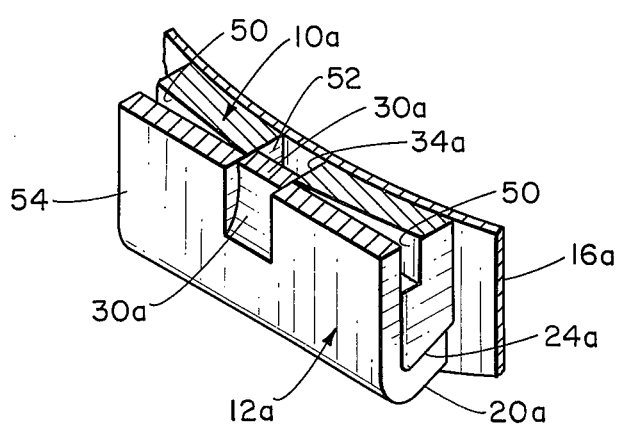

FIGS. 7 and 8 show a variation of the embodiment shown in FIGS. 5 and 6 in which the pedestal 10 has been rotated 90° so that the bracket base 12 slides on to the pedestal along a mesial-distal axis. In this embodiment a pair of ramps 50 are located respectively at each side of recess 52 so that the bracket member 12 may be slid onto the pedestal 10 from either side.

Figure 9:
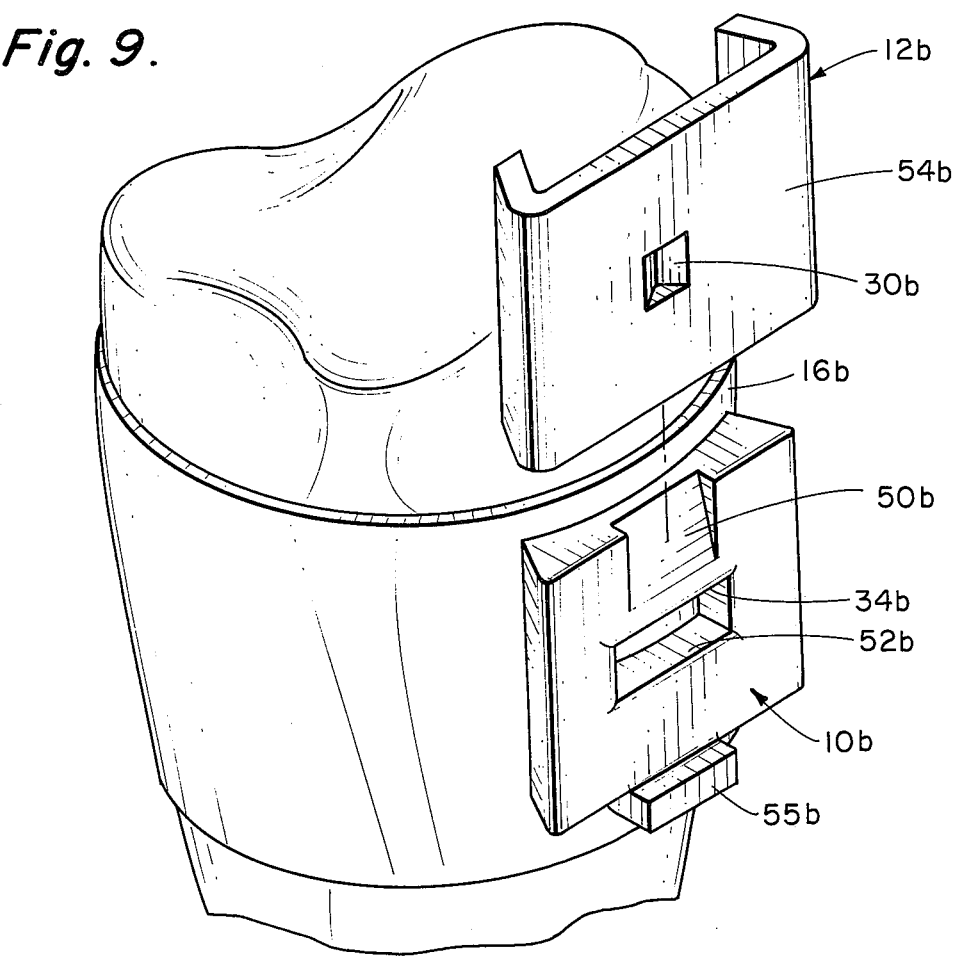
FIGS. 9 and 10 are views counterpart to FIGS. 4 and 6, respectively, showing a modified form thereof.
Figure 10:
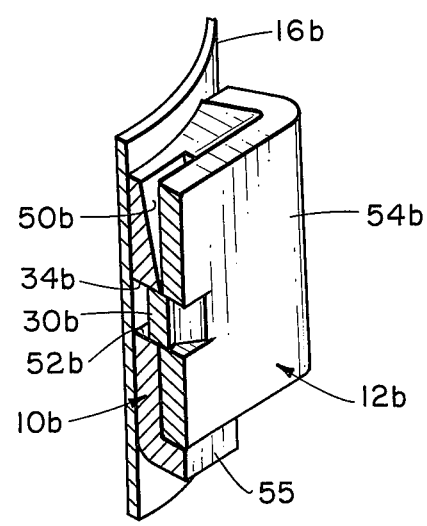

The form of the invention shown in FIGS. 9 and 10 is substantially the same as that shown in FIGS. 7 and 8, except that the detent 30b, which is embossed out of the bracket base 54b, is considerably shorter than the arc detent 30a. Thus, in this form of the invention, the flexing almost entirely takes place in the body of the two members 10b and 54b, with very little relative flexing between the detent 30b and its parent metal 54b.

In each case the flexing/bowing of the complete body portion is made possible by the central positioning of the recess 52, which allows optimum flexing of the entire body portion, as the embossed detent 30a (30b) rides up the ramp 50 (50b) and into the recess 52 (52b).

Whereas the invention has been shown and described herein in what is conceived to be the best mode contemplated, it is recognized that departures may be made therefrom within the scope of the invention which is therefore not to be limited to the details disclosed herein but is to be afforded the full scope of the invention.

What is claimed is:

1. Orthodontic appliance comprising:
a pedestal member adapted to be secured to a tooth;
a bracket member;
one of said members having a slide way;
the other of said members having a slide selectively receivable in said slide way, whereby said bracket member may be selectively applied to and removed from the tooth without removing said pedestal member;
a detent edge formed on a first one of said members;
an elongate locking member formed from a second one of said members, at least one end of said locking member being integrally joined to said second one of said members, the intermediate portion of said locking member being free of said second one of said members, so that it is free to flex as said members are slid together, and then drop over said edge, thereby to lock said members together.

2. Appliance in accordance with claim 1 wherein:
said detent edge is formed by a recess in said first one of said members;
said locking member is formed from said second one of said members by lancing out a portion of said second one of said members; and
said first one of said members includes sloping ramp means paralleling said slide and slide way for camming said locking member into said recess.

3. Appliance in accordance with claim 2 wherein:
said bracket member constitutes said second one of said members and is formed of two parts, a bracket base and a bracket lug, bonded together;
said bracket base comprising a relatively flat base member slideable onto said pedestal member and containing said lanced locking member;
said bracket lug being permanently bonded to said bracket base over said lanced-out locking member, and wherein:
said pedestal member comprises said first one of said members;
said recess being formed in the central portion of said pedestal member;
said ramp means extending from one edge of said pedestal portion inward to a point adjacent said recess, thereby to effect said camming of said locking member as said bracket member is slid onto said pedestal member.

4. Apparatus in accordance with claim 1 wherein said slide and slide way are oriented on the incisalgingival axis.

5. Appliance in accordance with claim 2 wherein:
said slide and slide way are oriented on the mesial-distal axis; and
said ramp means comprises a pair of ramps located respectively at each side of said recess, whereby said bracket member may be slid onto said pedestal member from either side of said pedestal member.

6. Appliance in accordance with claim 1 wherein:
said pedestal member has a keyway open at one end;
said locking member is formed as a finger extending transversely across the open end of say keyway;
said bracket member having a key slideable in said keyway;
said edge is constituted by the end of said key;
whereby in sliding said bracket member onto said pedestal member, said finger is deflected until it clears said edge and then drops over said edge to lock said members together.

7. Orthodontic appliance comprsing:
a pedestal member adapted to be secured to a tooth;
a bracket member;
one of said members having a slide way;
the other of said members having a slide slectively receivable in said slide way, whereby said bracket member may be slectively applied to and removed from the tooth without removing said pedestal member;
a recess in the central portion of a first one of said members;
a detent embossed from a second one of said members in the central portion thereof and engageable in said recess to detentably lock said members together;
said first one of said members having ramp means paralleling said slide and slide way;
said members being formed of material having sufficient resiliency to permit deflection thereof as said embossed detent slides up said ramp means before dropping into said recess.

8. Appliance according to claim 1 including:
stop means for stopping and retaining said bracket members after said members have been locked together.

9. Appliance according to claim 2 including:
stop means for stopping and retaining said bracket member after said members have been locked together.

10. Appliance according to claim 9 wherein:
said stop means comprises an integral bent-up portion on the edge of said first member opposite said sloping ramp.

* * * * *